US008440606B2

(12) United States Patent
Mundschau et al.

(10) Patent No.: US 8,440,606 B2
(45) Date of Patent: *May 14, 2013

(54) FOAMING HAND SPONGE FOR BODILY CLEANSING WITH COLOR CHANGE INDICATOR

(75) Inventors: Stacy Averic Mundschau, Weyauwega, WI (US); Scott W. Wenzel, Neenah, WI (US); Michael Ralph Lostocco, Appleton, WI (US); William Clayton Bunyard, DePere, WI (US); Jian Qin, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/777,134

(22) Filed: Jul. 12, 2007

(65) Prior Publication Data

US 2009/0018047 A1 Jan. 15, 2009

(51) Int. Cl.
*C11D 7/60* (2006.01)

(52) U.S. Cl.
USPC ............ 510/438; 510/236; 510/414; 510/416

(58) Field of Classification Search .................. 510/438, 510/238, 416, 414
See application file for complete search history.

(56) References Cited

U.S. PATENT DOCUMENTS

| | | | |
|---|---|---|---|
| 3,600,060 A | 8/1971 | Churchill | |
| 3,619,254 A | 11/1971 | Davis | |
| 3,855,046 A | 12/1974 | Hansen et al. | |
| 3,949,137 A | 4/1976 | Akrongold et al. | |
| 3,974,319 A | 8/1976 | Alibeckoff | |
| 4,022,706 A | 5/1977 | Davis | |
| 4,240,760 A | 12/1980 | Levine | |
| 4,659,609 A | 4/1987 | Lamers et al. | |
| 4,820,579 A | 4/1989 | Aszman | |
| 4,833,003 A | 5/1989 | Win et al. | |
| 5,431,697 A | 7/1995 | Kamata et al. | |
| 5,507,968 A | 4/1996 | Palaikis | |
| 5,620,779 A | 4/1997 | Levy et al. | |
| 5,640,737 A | 6/1997 | Boggs | |
| 5,683,971 A | 11/1997 | Rose et al. | |
| 5,744,150 A | 4/1998 | Cercone | |
| 5,962,112 A | 10/1999 | Haynes et al. | |
| 6,127,593 A * | 10/2000 | Bjorkquist et al. | 604/364 |
| 6,180,584 B1 * | 1/2001 | Sawan et al. | 510/382 |
| 6,296,929 B1 | 10/2001 | Gentile et al. | |
| 6,362,389 B1 * | 3/2002 | McDowall et al. | 604/367 |
| 6,380,151 B1 * | 4/2002 | Masters et al. | 510/438 |
| 6,485,822 B1 | 11/2002 | Osiecki et al. | |
| 6,550,633 B2 | 4/2003 | Huang et al. | |
| 6,663,306 B2 * | 12/2003 | Policicchio et al. | 401/138 |
| 6,838,154 B1 | 1/2005 | Varona et al. | |
| 6,958,103 B2 | 10/2005 | Anderson et al. | |
| 7,127,768 B2 | 10/2006 | Blum et al. | |
| 7,132,377 B2 | 11/2006 | Borgonjon et al. | |
| 7,192,896 B2 * | 3/2007 | Seth et al. | 442/400 |
| 2002/0090453 A1 | 7/2002 | Muthiah et al. | |
| 2003/0121530 A1 | 7/2003 | Borgonjon et al. | |
| 2003/0175418 A1 | 9/2003 | Muthiah et al. | |
| 2005/0005869 A1 | 1/2005 | Fritter et al. | |
| 2005/0118239 A1 * | 6/2005 | Sabesan | 424/443 |
| 2005/0136238 A1 * | 6/2005 | Lindsay et al. | 428/304.4 |
| 2005/0155631 A1 | 7/2005 | Kilkenny et al. | |
| 2005/0158364 A1 | 7/2005 | Yuksel et al. | |
| 2005/0202232 A1 * | 9/2005 | Sauniere | 428/316.6 |
| 2005/0229344 A1 | 10/2005 | Mittelstaedt et al. | |
| 2005/0244211 A1 | 11/2005 | Brunner et al. | |
| 2005/0260390 A1 | 11/2005 | Croft et al. | |
| 2005/0266229 A1 * | 12/2005 | Porticos et al. | 428/317.9 |
| 2006/0003912 A1 * | 1/2006 | Lindsay et al. | 510/267 |
| 2006/0134728 A1 | 6/2006 | MacDonald et al. | |
| 2006/0135026 A1 | 6/2006 | Arendt et al. | |
| 2006/0229219 A1 | 10/2006 | Bednarz et al. | |
| 2006/0287215 A1 | 12/2006 | McDonald et al. | |
| 2007/0134304 A1 * | 6/2007 | Aubrun-Sonneville et al. | 424/443 |
| 2007/0142263 A1 * | 6/2007 | Stahl et al. | 510/475 |
| 2008/0022940 A1 | 1/2008 | Kirsch et al. | |
| 2009/0018048 A1 | 1/2009 | Mundschau et al. | |

FOREIGN PATENT DOCUMENTS

| | | |
|---|---|---|
| KR | 100309307 B1 | 12/2001 |
| KR | 1020040078598 A | 9/2004 |
| KR | 1020040082321 A1 | 9/2004 |

OTHER PUBLICATIONS

Hitoshi, Tachino et al. Macromolecules 1994, 27, 372-378.*
Office Action dated Apr. 8, 2008 regarding U.S. Appl. No. 11/777,136, 11 pages.
International Search Report and Written Opinion from PCT/IB2008/052767, dated Mar. 16, 2009.
Non-final Office Action regarding U.S. Appl. No. 11/777,136, dated Feb. 23, 2009.
International Search Report and Written Opinion, PCT/IB2008/052765 (Feb. 26, 2009).
Final Office Action regarding U.S. Appl. No. 11/777,136, dated Jun. 12, 2009.
Office Action regarding U.S. Appl. No. 11/777,136, dated Sep. 18, 2009.
Final Office Action regarding U.S. Appl. No. 11/777,136, dated Apr. 5, 2010.
Final Office action issued in U.S. Appl. No. 11/777,136, dated Feb. 17, 2011.
Non-Final Office Action issued in U.S. Appl. No. 11/777,136, dated Apr. 28, 2011.
Non-final Office action received in U.S. Appl. No. 11/777,136 dated Mar. 26, 2012.
Examiner's First Report for Australian Patent Application No. 2008273751, mailed Feb. 1, 2012.
Final Office Action regarding U.S. Appl. No. 11/777,136, dated Aug. 2, 2012.
Final Office action issued in U.S. Appl. No. 11/777,136, dated Oct. 21, 2011.

* cited by examiner

*Primary Examiner* — Mark Eashoo
*Assistant Examiner* — M. Reza Asdjodi
(74) *Attorney, Agent, or Firm* — Armstrong Teasdale LLP

(57) ABSTRACT

A cleansing product suitable for making the cleaning of both inanimate and animate surfaces more fun and effective for children is disclosed. Specifically, the cleansing product is capable of expanding in volume under certain temperature conditions, and in some embodiments, can additionally include a coloring agent, providing a color change to indicate when sufficient cleansing has been performed.

14 Claims, 1 Drawing Sheet

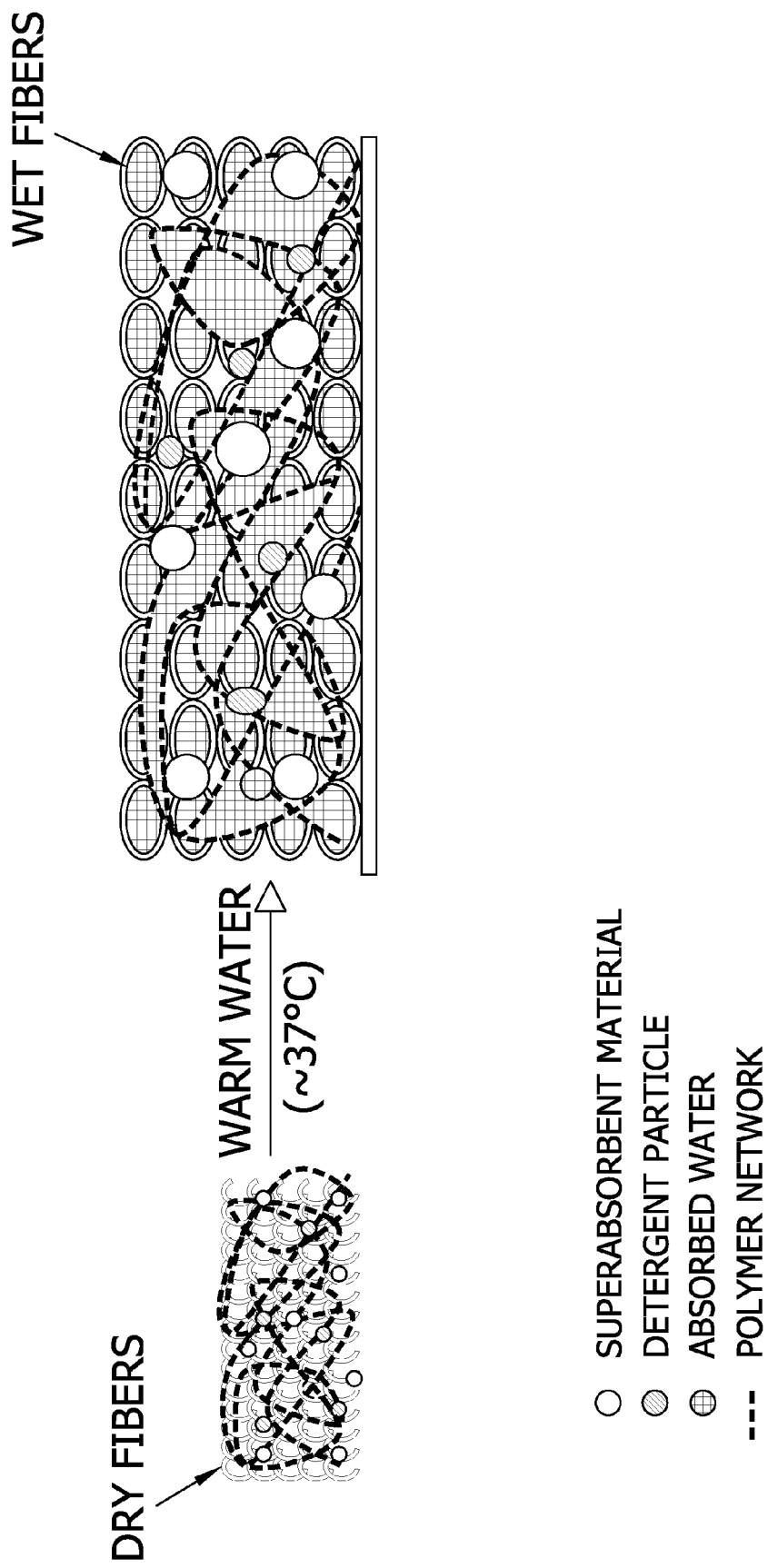

FOAMING HAND SPONGE FOR BODILY CLEANSING WITH COLOR CHANGE INDICATOR

BACKGROUND OF DISCLOSURE

The present disclosure generally relates to a cleansing product for cleaning both inanimate and animate surfaces capable of expanding in volume under certain temperature conditions. More particularly, the cleansing product is a hand sponge for cleaning hard surfaces or for cleansing the body. Furthermore, the hand sponge can additionally include a coloring agent, providing a color change to indicate when sufficient cleansing has been performed.

According to the Center for Disease Control, proper cleansing can be one of the most effective steps that can be taken to prevent the spread of diseases and infections. Specifically, proper bodily cleansing according to various sources requires not only using soap but also washing for a sufficiently long period of time in order to remove dirt and any microorganisms that may be present on the skin. For example, the Center for Disease Control has stated that cleaning should last at least 15 seconds.

Adults and children alike, however, tend to hurry through the task of washing and typically do not use soap, do not use a sufficient amount of soap, or do not rub a soap product over their skin for a sufficient length of time necessary to remove substantially all microorganisms that may be present.

Children in particular are known not to appreciate the importance of good hygiene and generally dislike the task of washing even though children continue to play in environments where microorganisms are freely transferred. Parents and other adults attempt to remind children continuously of the need to properly wash. Even with constant reminders, however, children continue to not wash properly unless an adult is actually present during the task. Adult supervision, however, is not often practical during every cleansing episode.

Similarly, children generally dislike participating in household chores which involve cleaning messes off of inanimate surfaces such as sinks, countertops, bathtubs, and tables. As such, many children fail to help with the chores at all or spend insufficient time washing the surfaces to ensure sanitary conditions have been attained.

As such, there is a need in the art to encourage children and adults alike to participate in proper cleansing practices and extend the amount of time spent on cleansing activities on both the skin and inanimate surfaces. Furthermore, it would be advantageous to have a cleansing product that could make cleaning fun for children. In this manner, parents and caretakers would be free from supervising every cleansing activity as they could be assured that their children were doing an adequate job.

SUMMARY OF THE DISCLOSURE

Generally, the present disclosure is directed to a cleansing product that is capable of making cleaning of the body and/or inanimate surfaces fun. Specifically, the cleansing product is capable of expanding in volume under certain temperature conditions. Typical cleansing products can expand to their full final volume within seconds of contacting water. One advantage of the cleansing product of the present disclosure, however, is that the swelling characteristics of the product are delayed to a minimum of about 10 second to provide a visual and tactile indicator to the user that sufficient time has passed during cleansing of the desired surface. In one embodiment, the cleansing product is additionally capable of stretching, thereby allowing more fun for children during cleansing activities. Specifically, the cleansing product comprises an absorbent material in which the volume of the material is initially constrained by a polymeric network. Once in contact with warm water, the product expands several fold from its original volume. In one particularly preferred embodiment, the cleansing product is a hand sponge for use in body cleansing and/or cleaning inanimate surfaces.

Furthermore, in one particularly preferred embodiment, the cleansing product can additionally include a coloring agent, providing a color change to indicate when sufficient cleansing has been performed. Specifically, color changing emblems or designs that act as a means to indicate the appropriate usage time for the cleansing activity could be impregnated or printed onto the cleansing product for additional consumer appeal and functionality.

As such, the present disclosure is directed to a cleansing product for bodily cleansing. The cleansing product comprises: an absorbent material, a polymeric network, an exfolliant agent, and a cleansing composition. The cleansing composition comprises a surfactant. The cleansing product is capable of expanding to a size of from about 80% to about 100% of its final expanded volume when contacted with warm water having a temperature of from about 19° C. to about 65° C. in no sooner than about 10 seconds.

The present disclosure is further directed to a cleansing product for cleaning a user's skin. The cleansing product comprises: an absorbent material, a polymeric network, an exfolliant agent, a coloring agent, and a cleansing composition. The cleansing composition comprises a surfactant. The cleansing product is capable of expanding to a size of from about 80% to about 100% of its final expanded volume when contacted with warm water having a temperature of from about 19° C. to about 65° C. in no sooner than about 10 seconds. The coloring agent is capable of changing the color of the cleansing product when the cleansing product is contacted with warm water in no sooner than 15 seconds.

Other objects and features will be in part apparent and in part pointed out hereinafter.

BRIEF DESCRIPTION OF THE DRAWINGS

FIG. 1 depicts a cleansing product that has expanded in volume upon contact with warm water as set forth in one embodiment of the present disclosure.

DETAILED DESCRIPTION OF THE DISCLOSURE

The present disclosure is directed to a cleansing product that is capable of making cleaning of the body and/or inanimate surfaces fun by expanding in volume under certain temperature and time conditions such as when the cleansing product is contacted with warm water. In one embodiment, the cleansing product is a bodily cleansing product for use in exfoliating, cleansing, and conditioning the skin or a user.

Specifically, the cleansing product comprises an absorbent material in which the volume of the material is initially constrained by a polymeric network. Once the temperature of the cleansing product is increased, such as by contacting the product with warm water, the absorbent product expands several fold from its original volume. Typically, in order for the cleansing product to expand, the temperature of the product should increase to a temperature of from about 19° C. (66.2° F.) to about 65° C. (149° F.). More suitably, the temperature of the cleansing product should increase to a temperature of from about 23° C. (73.4° F.) to about 42° C. (107.6° F.).

Typically, the cleansing products comprise from about 10% (by weight) absorbent material to about 99% (by weight) absorbent material. More suitably, the cleansing products comprise from about 40% (by weight) absorbent material to about 90% (by weight) absorbent material and, even more suitably, from about 60% (by weight) absorbent material to about 90% (by weight) absorbent material.

Suitable materials for use as the absorbent material in the cleansing product include any non-woven web materials, woven materials, knit materials, wet-strength papers, extrusion and emulsion-based products, or combinations thereof that have sufficient wet strength and integrity to hold an effective amount of fluid. In a particularly preferred embodiment, the absorbent material is a non-woven web material. Suitable non-woven web materials include meltblown webs, spunbonded webs, bonded carded webs, wet-laid webs, airlaid webs, coform webs, hydraulically entangled webs, and combinations thereof. In addition, non-woven webs may contain synthetic fibers (e.g., polyethylenes, polypropylenes, polyvinyl chlorides, polyvinylidene chlorides, polystyrenes, polyesters, polyamides, polyimides, etc.). If desired, the non-woven web may also be bonded using techniques well known in the art to improve the durability, strength, hand, aesthetics, texture, and/or other properties of the fabric. For instance, the non-woven web may be thermally (e.g., pattern bonded), ultrasonically, adhesively and/or mechanically (e.g., through-air dried) bonded. For instance, various pattern bonding techniques are described in U.S. Pat. No. 3,855,046 to Hansen; U.S. Pat. No. 5,620,779 to Levy, et al; and U.S. Pat. No. 5,962,112 to Haynes et al., which are all incorporated herein by reference to the extent they are consistent herewith.

The non-woven web may be bonded by continuous seams or patterns. As additional examples, the non-woven web may be bonded along the periphery of the sheet or simply across the width or cross-direction of the web adjacent to the edges. Other bonding techniques, such as a combination of thermal bonding and latex impregnation, may also be used. Alternatively and/or additionally, a resin, latex or adhesive may be applied to the non-woven fabric by, for example, spraying or printing, and dried to provide the desired bonding.

If desired, the non-woven web may also be imparted with texture on one or more of its surfaces. For instances, techniques for forming dual-textured spunbonded or meltblown materials are described in U.S. Pat. No. 4,659,609 to Lamers, et al. and U.S. Pat. No. 4,833,003 to Win, et al., which are both incorporated herein by reference to the extent they are consistent herewith.

Additionally, the absorbent material of the cleansing product can optionally include an elastomeric random block polymer. The elastomeric polymer may impart additional stretch characteristics to the absorbent material, allowing for expansion in volume to a greater extent. Suitable elastomeric random block polymers include, for example, styrene-butylene-styrene (SBS) polymers, styrene-ethylene/butylene-styrene (SEBS) polymers, styrene-ethylene/propylene-styrene (SEPS), and combinations thereof, all commercially available as Kraton polymers (from Kraton, Houston, Tex.). Additional elastomeric random block polymers for use in the cleansing product can include semi-crystalline polyolefin polymers, such as commercially available from ExxonMobil (Houston, Tex.) under the tradename Vistamaxx®.

Typically, when used in the absorbent material of the cleansing product, the elastomeric random block polymers are present in the absorbent material in an amount of from about 5% (by total weight absorbent material) to about 15% (by total weight absorbent material).

In one particularly preferred embodiment, the absorbent material includes superabsorbent material, alone or in combination with one or more of the absorbent materials described above. When in combination with the absorbent materials described above, the superabsorbent material is typically either coated onto the absorbent material or blended with the absorbent material using coforming processes. It has been found that suitable superabsorbent materials for use in the present cleansing product can generate a high amount of expansion pressure, which can further increase the amount and rate of volume expansion of the cleansing product. Additionally, superabsorbent materials with a delayed swelling characteristic can be used to control the overall rate at which the cleansing product swells. This would be advantageous as a visual cue as the fully expanded web would indicate enough time has been spent cleaning the desired surface. Suitable superabsorbent materials that can display this delayed swelling behavior include non-ionic superabsorbent materials, ionic superabsorbent materials, as well as coated or encapsulated superabsorbent materials. Examples of non-ionic superabsorbent materials include crosslinked poly(ethylene oxide), polyvinyl alcohol, hydroxyalkyl cellulose, guar gum, gelatin, and poly(vinyl pyrrolidone). Examples of ionic superabsorbent materials include carboxylate-functional, phosphate-functional, sulfonate-functional, amino-functional, and quaternary ammonium-functional superabsorbent materials. An example of a suitable encapsulation superabsorbent material would be a core of high swelling poly(sodium acrylate) surrounded by swelling poly(acrylic acid). In this latter example, the difference in the sodium ions between the layers would mediate the swelling of the shell without significantly reducing the ultimate swellability of the core. Generally, under such circumstances, larger superabsorbent particles (e.g., having low surface area) would be preferred over smaller particles due to the lower overall proportion of the surface area relative to the total volume.

Additional superabsorbent materials suitable for use in the present disclosure are known to those skilled in the art, and may be in any operative form, such as a superabsorbent solution. Generally, the solution contains solid material including an uncrosslinked linear superabsorbent polymer and a latent crosslinking agent that can either be copolymerized onto the superabsorbent polymer chains or physically blended into the solution. Typically, the superabsorbent solution contains no more than about 20% (by total weight superabsorbent solution) solids. More suitably, the superabsorbent solution contains from about 0.1% (by total weight superabsorbent solution) to about 20% (by total weight superabsorbent solution) and, even more suitably, from about 1% (by total weight superabsorbent solution) to about 10% (by total weight superabsorbent solution).

In another embodiment, the superabsorbent material is in particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, chitan protein, and guar gum; modified natural materials such as carboxymethyl cellulose, carboxyethyl cellulose, and hydroxypropyl cellulose, chitosan; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, polyvinylamine, polyquaternary ammonium, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc.

In yet another embodiment, the superabsorbent material may be in the form of a film material. Superabsorbent films can be produced by either casting or extruding superabsorbent precursor solutions at various concentrations. The thickness of the films can be controlled by the solution concentration and die opening. Typically, superabsorbent precursor solutions are prepared by mixing one or more monomers with an initiating and neutralizing agent in the presence of a chemical crosslinking agent. The ingredients and procedures for producing a superabsorbent precursor solution are well known in the art. Particularly preferred examples of superabsorbent film materials include sodium polyacrylates and carboxymethylcellulose film materials.

The superabsorbent film materials, when used, may be either layered or non-layered film materials.

Other forms of superabsorbent material include, without limitation, superabsorbent fiber materials, superabsorbent non-woven materials, superabsorbent foams, and combinations thereof.

Typically, when superabsorbent material is used in the absorbent material of the cleansing product of the present disclosure, the superabsorbent material is present in an amount of from about 0.1% (by total weight absorbent material) to about 20% (by total weight absorbent material). More suitably, the superabsorbent material is present in the amount of from about 0.1% (by total weight absorbent material) to about 10% (by total weight absorbent material) and, even more suitably about 0.1% (by total weight absorbent material) to about 5.0% (by total weight absorbent material).

In another particularly preferred embodiment, a sponge material can be used in the cleansing product either alone, or in combination with one or more of the above-described absorbent materials. Typically, the sponge material can be incorporated randomly with one or more of the absorbent materials or can be layered throughout the absorbent materials. For example, in one suitable embodiment, the cleansing product includes a single layer having a mixture of absorbent material and sponge material. This mixture is then compressed using the polymeric network described more fully below. In an alternative suitable embodiment, the cleansing product will consist of a first layer of absorbent material (and polymeric network) and a second layer of sponge material.

Suitable sponge material can include, for example, blocks of melamine foam. Melamine-based foam material has an open-celled, microporous structure. The material has been found to be abrasive in that when rubbed across the surface, direct and other unwanted elements will be removed. Particles of melamine-foam material may break off due to this abrasive contact. Over time, the melamine-foam material will be worn down due to repeated abrasion with the surface to be cleaned and the unwanted elements present on the surface.

Another suitable sponge material includes cellulose material. Suitable cellulose materials are, for example, absorbent cellulosic materials, such as, wood pulp fibers. Suitable commercially available cellulosic fibers for use in the cleansing products can include, for example NF405, which is a chemically treated bleached southern softwood Kraft pulp, available from Weyerhaeuser Co. of Federal Way (Washington); NB 416, which is a bleached southern softwood Draft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.); Sodra Red, a chemi-thermo-mechanical pulp (BCTMP), available from Sodra Cell Folla, S.A. (Follafoss, Norway).

Other sponge materials suitable for use in the cleansing product can include polyurethane, latex, thermoplastics (e.g., polyethylene, polypropylene, polyester, and polyamide copolymers), and combinations thereof.

The relative percentages of the absorbent material and sponge material can vary over a wide range depending upon the desired characteristics of the cleansing product.

In addition to the absorbent material, the cleansing product of the present disclosure includes a polymeric network to contain the absorbent material. Typically, the polymeric network helps to maintain a compressed shape of the cleansing product at a lower overall volume at room temperature (i.e., approximately, 23° C. (73.4° F.)) before use and immediately upon contact with warm water during use. Specifically, the polymeric network forms to entrap the absorbent material, thereby keeping the absorbent material compressed. The polymeric network may constrain the absorbent material by incorporation (e.g., impregnating the polymeric network into absorbent material) throughout the absorbent material itself or it may constrain the absorbent material through complete or partial encapsulation of the absorbent material within the overall structure of the cleansing product.

The polymeric network thus works to retard the inherent expansion rate of the absorbent material used in the cleansing product when contacted with warm water so that the final expanded volume of the cleansing product is achieved after the desired amount of time when exposed to excess warm water. To accomplish this, the polymeric network is chosen such that it has a water-dissolution, water-swelling, and/or water-softening rate tailored to the desired expansion rate of the absorbent material. More specifically, the polymeric network is designed such that it provides a significantly faster expansion rate and greater final expanded volume of the absorbent material in warm water versus cool water over the expected use time of the cleansing product. As used herein, the term "warm water" refers to water having a temperature of from about 19° C. to about 65° C. and, more suitably, refers to water having a temperature of from about 23° C. to about 46° C. The water-dissolution or water-swelling rate of the polymeric network would be faster in warm water than in cold water and the final expanded volume of the absorbent material would be greater in warm water than in cold water within the expected use time of the cleansing product. A significantly faster cleansing product expansion rate and final expanded volume in warm water versus cold water would encourage the child to use warm water for cleansing activities as compared to cold water.

The temperature dependent volume expansion of the cleansing product is controlled through the selection of a polymeric network with the appropriate hydrophilicity, glass transition temperature (Tg), degree of crystallinity and melting temperature (if semicrystalline) to achieve the aforementioned control of water-dissolution, water-swelling, and/or water-softening rates. Specifically, in one preferred embodiment, the polymers for use in the polymeric network are polymers having an amorphous or low (e.g., partial) crystallinity structure and a low melting temperature. Specifically, if the polymers comprising the polymer network are semicrystalline, the crystallinity of the polymers selected should be sufficiently low, and the melting temperature should be sufficiently low, so as not to impede swelling of the polymer once the cleansing product is contacted with warm water. As such, suitably, the melting temperature of a semicrystalline polymeric network should be less than about 65° C., more suitably less than about 42° C. and, even more suitably, less than about 30° C.

Polymers having the characteristics suitable for use in the polymeric network include, for example, fully-hydrolyzed polyvinyl alcohol, partially-hydrolyzed polyvinyl alcohol, modified polyvinyl alcohol, starch, modified starches, acid/acrylate copolymers, styrene maleic anhydride copolymer, ethylene acrylic acid copolymer, metal salt neutralized ethylene methacrylic acid copolymer, polyether block amide copolymer, polyether-block-polyurethane, polyethylene oxide, water-soluble polyester, water-soluble copolyester, polyethyloxazoline, water-soluble polyurethane, polyacrylamides, and combinations thereof.

The polymeric network may comprise at least one, but may also comprise multiple, polymeric compositions to control the desired expansion rate of the absorbent/superabsorbent material.

With the use of the polymeric network as described above, the expansion of the cleansing product (and, more specifically, the absorbent material) is prevented until the cleansing product is contacted with warm water for a predetermined time period. Once contacted with warm water, the cleansing product is capable of expanding to a size of from about 80% to about 100% of its final expanded volume and, more suitably, from about 90% to about 100% of its final expanded volume, no sooner than about 10 seconds after being contacted with warm water. More suitably, the cleansing product is capable of expanding to a size of from about 80% to about 100% of its final expanded volume and, more suitably, from about 90% to about 100% of its final expanded volume, after about 15 seconds and, even more suitably, after about 20 seconds.

In an another embodiment, the polymers for use in the polymeric network have a glass transition temperature greater than ambient temperature (approximately 23° C.) or the storage temperature of the cleansing product. A glass transition temperature greater than ambient storage temperature of the cleansing product allows the polymeric network to maintain a compressed state of the absorbent material while it is dry and before contact with excess warm water. Maintaining a more compressed state while dry helps to increase the overall expanded volume achieved upon contact with excess warm water. Optionally, plasticizing agents can be used to lower the glass transition temperature of a particular polymer used in the polymeric network to achieve the desired material properties (i.e., stiffness). Polymers or polymer/plasticizer combinations having these higher glass transition temperatures that are suitable for use in the cleansing products of the present disclosure include, for example, those polymers having a glass transition temperature of greater than 20° C. (68° F.). More suitably, the polymers or polymer/plasticizer combinations have a glass transition temperature greater than about 30° C. (86° C.) and, even more suitably, greater than about 40° C. (104° F.).

Typically, to constrain the absorbent material of the cleansing product in the desired amount, the polymeric network is present in the cleansing product in an amount of no greater than 50% (by total weight product). More suitably, the polymeric network is present in the cleansing product in an amount of no greater than 30% (by total weight product) and, even more suitably, no greater than 5% (by total weight product).

In addition to the expanding absorbent material, the cleansing product suitably may be a fun product for children by incorporating coloring agents for producing a change of color in the product during use. Specifically, the coloring agent is configured to change the color of the cleansing product as the temperature of the cleansing product is increased or as the cleansing product begins to absorb liquid such as water. Specifically, when the cleansing product is used, the temperature of the cleansing product may increase due to contact with the user, due to friction that is caused during washing or scrubbing a surface, and/or due to the presence of warm water. In accordance with the present disclosure, once the cleansing product reaches a selected temperature, the cleansing product and its coloring agent can be configured to either initiate a color change or discontinue a changing color, indicating to the user that the user has spent sufficient time washing, wiping, or scrubbing. The coloring agent in one embodiment of the present disclosure, for instance, may comprise leuco dyes. For example, when the cleansing product is intended to be used to clean at least a portion of a person's body, the coloring agent present in the cleansing product may be configured to change the color of the product as the product is heated to temperatures of from about 21° C. (69.8° F.) to about 65° C. (149° F.), such as from about 23° C. (73.4° F.) to about 38° C. (100.4° F.), and such as, in one embodiment, from about 25° C. (77° F.) to about 36° C. (96.8° F.).

When the cleansing product is used to clean inanimate hard surfaces, on the other hand, the temperature at which the color change is activated may be lower or higher than the temperatures provided above.

The coloring agent contained within the cleansing product may be configured to change the color of the product in various ways. For example, in one embodiment, once the product reaches a selected temperature, the product may change from a base color to a white or a clear color. Specifically, in this embodiment, the coloring agent is capable of changing the color of the cleansing product when the cleansing product is contacted with warm water in no sooner than 15 seconds. More suitably, the coloring agent is capable of changing the color of the cleansing product when the cleansing product is contacted with warm water in no sooner than 20 seconds and, even more suitably, no sooner than 25 seconds.

In another embodiment, a pigment or dye that does not change color based on temperature may be present in the cleansing product for providing a base color. The coloring agents, on the other hand, can be included in order to change the product from the base color to at least one other color. As in the above embodiment, the coloring agent (e.g., pigment or dye) is capable of changing the color of the cleansing product when the cleansing product is contacted with warm water in no sooner than 15 seconds. More suitably, the coloring agent is capable of changing the color of the cleansing product when the cleansing product is contacted with warm water in no sooner than 20 seconds and, even more suitably, no sooner than 25 seconds.

Alternatively or, in addition to, the coloring agent may be configured to react with the other ingredients of the cleansing product to cause a color change. Specifically, for example, the coloring agent could produce a colored cleansing product, the color of which would fade during cleaning to indicate a desired length of time has passed. In one embodiment, the surfactant in the cleansing composition (as described below) could solubilize the coloring agent, resulting in a fading or complete disappearance of the color.

Generally, there are two classes of coloring agents for use in the cleansing products of the present disclosure. Specifically, the first class includes dyes, pigments, and lakes. Dyes suitable for use in the cleansing product can include, for example, FD&C orange #5, FD&C yellow #10, FD&C green #3, and FD&C blue #1.

As noted above, lakes and pigments can also be used in the cleansing product to produce a desired color change. Suitable lakes and pigments include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

In general, the coloring agents may be present in the cleansing product in an amount from about 0.001% (by total weight product) to about 9% (by total weight product). Suitably, the coloring agents are present in the cleansing product in an amount of from about 0.01% (by total weight product) to about 3% (by total weight product and, even more suitably, about 1% (by total weight product).

The coloring agents of this first class are typically comprised of water soluble compounds. As such, when the cleansing product is contacted with water, the soluble coloring agents begin to solubilize and fade in color, causing the color of the cleansing product to ultimately fade or completely disappear. In another embodiment, some of these types of coloring agents, such as pigments, can become diluted as water is contacted with the cleansing product, causing the color to fade or disappear.

In one embodiment, the coloring agents are incorporated into the cleansing product in a pattern for creating a colored emblem or design on the product during use. Suitable patterns of coloring agents can include, for example, lines, swirls, dots, and the like, and emblems such as shapes, characters, symbols, and the like.

Furthermore, the coloring agent of this first class may optionally be encapsulated. Encapsulation can help ensure that the coloring agent is not prematurely solubilized or diluted by water, causing a premature color change. In one particularly preferred embodiment, the coloring agents are microencapsulated in a shell-type material that will dissolve, disintegrate, rupture, or otherwise breakdown upon contact with warm water and/or the cleansing composition to allow for the release of the coloring agent during washing or scrubbing with the cleansing product. Suitable microencapsulated shell materials are known in the art and include cellulose-based polymeric materials (e.g., ethyl cellulose), lactic acid-based aliphatic polyesters, carbohydrate-based materials (e.g., cationic starches and sugars) and materials derived therefrom (e.g., dextrins and cyclodextrins) as well as other materials compatible with human tissues.

Typically, the resulting microcapsules of coloring agent have a size of from about 1 to about 50 micrometers and, more suitably, from about 3 to about 15 micrometers.

In another embodiment to prevent premature activation of the coloring agent, the coloring agent can spatially be separated from the other ingredients in the cleansing product. For example, in one specific embodiment, the absorbent material of the cleansing product has an outer surface and an inner surface and the coloring agent is incorporated onto the outer surface of the absorbent material, while the cleansing composition, including one or more surfactants, is incorporated within the inner surface of the material.

In another particularly preferred embodiment, the absorbent material of the cleansing product can further comprise a porous non-woven layer placed in between its outer surface and its inner surface to prevent premature contact between the coloring agent and the surfactant of the cleansing composition as described more fully below. Suitable non-woven materials for use as the porous non-woven layers can include, for example, bonded-carded webs, spunbond webs and melt-blown webs, polyesters, polyolefins such as polypropylenes and polyethylenes, combinations of these materials or other suitable materials. While it is discussed herein that the absorbent material of the cleansing product may have a single layer of porous non-woven between its outer surface and its inner surface, it should be understood by one skilled in the art that the absorbent material of the cleansing product may have multiple non-woven layers to better ensure that the coloring agent is not prematurely exposed to the other components of the cleansing product, such as the surfactant, or control the overall rate of coloring agent dissolution. Specifically, the absorbent material of the cleansing product may include two porous non-woven layers between its outer surface and its inner surface, more suitably, the absorbent material may include three porous non-woven layers, even more suitably, four porous non-woven layers and, even more suitably, five or more porous non-woven layers.

In one particularly preferred embodiment using a coloring agent in the cleansing product, the cleansing product can further include one or more film materials laminated to one outer surface of the cleansing product to protect the coloring agent from mechanical abrasion or surfactant attach.

The film material can be secured to the outer surface of the cleansing product by, for example, thermal bonding or by a suitable laminating adhesive composition.

Thermal bonding includes continuous or discontinuous bonding using a heated roll. Point bonding is one suitable example of such a technique. Thermal bonds should also be understood to include various ultrasonic, microwave, and other bonding methods wherein the heat is generated in the film.

In a preferred embodiment, the film material and one outer surface of the cleansing product are laminated together using a water insoluble adhesive composition. Suitable water insoluble adhesive compositions can include hot melt adhesives and latex adhesives as described in U.S. Pat. No. 6,550,633, issued to Huang, et al. (Apr. 22, 2003); U.S. Pat. No. 6,838,154, issued to Anderson, et al. (Oct. 25, 2005); and U.S. Pat. No. 6,958,103, issued to Varona et al. (Jan. 4, 2005), which are hereby incorporated by reference to the extent they are consistent herewith. Suitable hot melt adhesives can include, for example, RT 2730 APAO and RT 2715 APAO, which are amorphous polyalphaolefin adhesives (commercially available from Huntsman Polymers Corporation, Odessa, Tex.) and H2800, H2727A, and H2525A, which are all styrenic block copolymers (commercially available from Bostik Findley, Inc., Wauwatosa, Wis.). Suitable latex adhesives include, for example, DUR-O-SET E-200 (commercially available from National Starch and Chemical Co., Ltd., Bridgewater, N.J.) and Hycar 26684 (commercially available from B. F. Goodrich, Laval, Quebec). Typically, the adhesive composition can be applied to the desired area by spraying, knifing, roller coating, or any other means suitable in the art for applying adhesive compositions.

Suitably, the adhesive composition can be applied to the desired area of the film material in an amount of from about 0.01 grams per square meter to about 20 grams per square meter. More suitably, the adhesive composition can be applied in an amount of from about 0.05 grams per square meter to about 5.0 grams per square meter.

The second class of suitable coloring agents for use in the cleansing products includes thermochromic agents. Thermochromic agents typically undergo a color change as the temperature of the cleansing product reaches a selected temperature. Suitably, the thermochromatic agent that can be used in the cleansing product of the present invention is capable of changing the color of the cleansing product when the agent is exposed to water having a temperature of from about 3° C. to about 45° C.

One particularly preferred thermochromic agent includes liquid crystals. The wavelength of light ("color") reflected by liquid crystals depends in part on the pitch of the helical structure of the liquid crystal molecules. Because the length of this pitch varies with temperature, the color of the liquid crystals is also a function of temperature. One particular type of liquid crystal that may be used in the present disclosure is a liquid crystal cholesterol derivative. Exemplary liquid crystal cholesterol derivatives may include alkanoic and aralkanoic acid esters of cholesterol, alkyl esters of cholesterol carbonate, cholesterol chloride, cholesterol bromide, cholesterol acetate, cholesterol oleate, cholesterol caprylate, cholesterol oleyl-carbonate, and so forth. Other suitable liquid crystal cholesterol derivatives are described in U.S. Pat. No. 3,600,060 to Churchill, et al.; U.S. Pat. No. 3,619,254 to Davis; and U.S. Pat. No. 4,022,706 to Davis, which are incorporated by reference to the extent they are consistent herewith.

In addition to liquid crystals, another suitable thermochromic agent that may be employed in the present disclosure is a composition that includes a proton accepting chromogen ("Lewis base") and a solvent. The melting point of the solvent controls the temperature at which the chromogen will change color. More specifically, at a temperature below the melting point of the solvent, the chromogen generally possesses a first color (e.g., red). When the solvent is heated to its melting temperature, the chromogen may become protonated or deprotonated, thereby resulting in a shift of the absorption maxima. The nature of the color change depends on a variety of factors, including the type of proton-accepting chromogen utilized and the presence of any additional temperature-insensitive chromogens. Regardless, the color change is typically reversible.

Although not required, the proton-accepting chromogen is typically an organic dye, such as a leuco dye. In solution, the protonated form of the leuco dye predominates at acidic pH levels (e.g., pH of about 4 or less). When the solution is made more alkaline through deprotonation, however, a color change occurs. Of course, the position of this equilibrium may be shifted with temperature when other components are present. Suitable leuco dyes for use in the present disclosure may include, for instance, phthalides; phthalanes; substituted phthalides or phthalanes, such as triphenylmethane phthalides, triphenylmethanes, or diphenylmethanes; acyl-leucomethylene blue compounds; fluoranes; indolylphthalides, spiropyranes; cumarins; and so forth. Exemplary fluoranes include, for instance, 3,3'-dimethoxyfluorane, 3,6-dimethoxyfluorane, 3,6-di-butoxyfluorane, 3-chloro-6-phenylamino-flourane, 3-diethylamino-6-dimethylfluorane, 3-diethylamino-6-methyl-7-chlorofluorane, and 3-diethyl-7,8-benzofluorane, 3,3'-bis-(p-dimethyl-aminophenyl)-7-phenylaminofluorane, 3-diethylamino-6-methyl-7-phenylaminofluorane, 3-diethylamino-7-phenylaminofluorane, and 2-anilino-3-methyl-6-diethylamino-fluorane. Likewise, exemplary phthalides include 3,3',3''-tris(p-dimethylaminophenyl)phthalide, 3,3'-bis(p-dimethyl-aminophenyl)phthalide, 3,3-bis(p-diethylamino-phenyl)-6-dimethylamino-phthalide, 3-(4-diethylaminophenyl)-3-(1-ethyl-2-methylindol-3-yl)phthalide, and 3-(4-diethylamino-2-methyl)phenyl-3-(1,2-dimethylindol-3-yl)phthalide.

Although any solvent for the thermochromic dye may generally be employed in the present disclosure, it is typically desired that the solvent have a low volatility. For example, the solvent may have a boiling point of about 150° C. or higher, and in some embodiments, from about 170° C. to 280° C. Likewise, the melting temperature of the solvent is also typically from about 25° C. to about 40° C., and in some embodiments, from about 30° C. to about 37° C. Examples of suitable solvents may include saturated or unsaturated alcohols containing about 6 to 30 carbon atoms, such as octyl alcohol, dodecyl alcohol, lauryl alcohol, cetyl alcohol, myristyl alcohol, stearyl alcohol, behenyl alcohol, geraniol, etc.; esters of saturated or unsaturated alcohols containing about 6 to 30 carbon atoms, such as butyl stearate, methyl stearate, lauryl laurate, lauryl stearate, stearyl laurate, methyl myristate, decyl myristate, lauryl myristate, butyl stearate, lauryl palmitate, decyl palmitate, palmitic acid glyceride, etc.; azomethines, such as benzylideneaniline, benzylidenelaurylamide, o-methoxybenzylidene laurylamine, benzylidene p-toluidine, p-cumylbenzylidene, etc.; amides, such as acetamide, stearamide, etc.; and so forth.

The thermochromic agent may also be included in the cleansing product in combination with a proton-donating agent (also referred to as a "color developer") to facilitate the reversibility of the color change. Such proton-donating agents may include, for instance, phenols, azoles, organic acids, esters of organic acids, and salts of organic acids. Exemplary phenols may include phenylphenol, bisphenol A, cresol, resorcinol, chlorolucinol, b-naphthol, 1,5-dihydroxynaphthalene, pyrocatechol, pyrogallol, trimer of p-chlorophenol-formaldehyde condensate, etc. Exemplary azoles may include benzotriaoles, such as 5-chlorobenzotriazole, 4-laurylaminosulfobenzotriazole, 5-butylbenzotriazole, dibenzotriazole, 2-oxybenzotriazole, 5-ethoxycarbonylbenzotriazole, etc.; imidazoles, such as oxybenzimidazole, etc.; tetrazoles; and so forth. Exemplary organic acids may include aromatic carboxylic acids, such as salicylic acid, methylenebissalicylic acid, resorcylic acid, gallic acid, benzoic acid, p-oxybenzoic acid, pyromellitic acid, b-naphthoic acid, tannic acid, toluic acid, trimellitic acid, phthalic acid, terephthalic acid, anthranilic acid, etc.; aliphatic carboxylic acids, such as stearic acid, 1,2-hydroxystearic acid, tartaric acid, citric acid, oxalic acid, lauric acid, etc.; and so forth. Exemplary esters may include alkyl esters of aromatic carboxylic acids in which the alkyl moiety has 1 to 6 carbon atoms, such as butyl gallate, ethyl p-hydroxybenzoate, methyl salicylate, etc.

When used, the amount of the proton-accepting chromogen employed may generally vary, but is typically from about 2% (by total weight thermochromatic agent) to about 20% (by total weight thermochromatic agent), and in some embodiments, from about 5% (by total weight thermochromatic agent) to about 15% (by total weight thermochromatic agent). Likewise, the proton-donating agent may constitute from about 5% (by total weight thermochromatic agent) to about 40% (by total weight thermochromatic agent), and more suitably, from about 10% (by total weight thermochromatic agent) to about 30% (by total weight thermochromatic agent). In addition, the solvent may constitute from about 50% (by total weight thermochromatic agent) to about 95% (by total weight thermochromatic agent), and more suitably, from about 65% (by total weight thermochromatic agent) to about 85% (by total weight thermochromatic agent).

Regardless of the particular thermochromic agent employed, it may be microencapsulated to enhance the stability of the agent during processing, similar to the dyes, lakes, and pigments, described above. For example, the thermochromic agent may be mixed with a thermosetting resin according to any conventional method, such as interfacial polymerization, in-situ polymerization, and the like. The thermosetting resin may include, for example, polyester resins, polyurethane resins, melamine resins, epoxy resins, diallyl phthalate resins, vinylester resins, and the like. The resulting mixture may then be granulated and optionally coated with a hydrophilic macromolecular compound, such as alginic acid and salts thereof, carrageenan, pectin, gelatin and the like, semisynthetic macromolecular compounds such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, and so forth. The resulting thermochromic microcapsules typically have a size of from about 1 to about 50 micrometers, and in some embodiments, from about 3 to about 15 micrometers. Various other microencapsulation techniques may also be described in U.S. Pat. No. 4,957,949 to Kamada, et al. and U.S. Pat. No. 5,431,697 to Kamada, et al., which are incorporated herein by reference to the extent they are consistent herewith. Suitable microencapsulated thermochromic substances may also be obtained from Matsui Shikiso Chemical Co., Ltd. of Kyoto, Japan under the designation "Chromicolor."

Thermochromic agents are commercially available from various sources. In one embodiment, for instance, thermochromic dyes marketed by Chromatic Technologies, Inc. of Ithaca, N.Y. may be incorporated into the cleansing product.

The thermochromic agents may be present in the cleansing product in an amount sufficient to have a visual effect on the color of the product. The amount or concentration of the agents can also be increased or decreased depending upon the desired intensity of any color. In general, the thermochromic agents may be present in the cleansing product in an amount from about 0.01% by weight to about 9% by weight, such as from about 0.1% by weight to about 3% by weight. For instance, in one particular embodiment, the thermochromic agents may be present in an amount about 1% by weight.

As described above, thermochromic agents typically change from a specific color to clear at a certain temperature. If desired, other pigments or dyes, such as those described more fully above, can be added to the cleansing products in order to provide a background color that remains constant independent of the temperature of the product. By adding other pigments or dyes in combination with the thermochromic agents to the cleansing product, the thermochromic agents can provide a color change at certain temperatures rather than just a loss of color should the thermochromic agent become clear. For instance, a pigment, such as a yellow pigment, may be used in conjunction with a plurality of thermochromic agents, such as a red thermochromic dye and a blue thermochromic dye. When all combined together, the cleansing product may have a dark color. As the product is increased in temperature, the red thermochromic dye may turn clear changing the color to a green shade (a combination of yellow and blue). As the temperature further increases, the blue thermochromic dye turns clear causing the cleansing product to turn yellow indicating to a user that a sufficient amount of washing has occurred.

It should be understood, that all different sorts of thermochromic agents and non-thermochromic pigments and dyes may be combined in order to produce a cleansing product having a desired base color and one that undergoes desired color changes. The color changes, for instance, can be somewhat dramatic and fanciful. For instance, in one embodiment, the cleansing composition may change from green to yellow to red, such as the colors of a stop light, during a washing operation. Once the color of the product turns red, a user would understand that sufficient time has elapsed and that the washing process is complete.

In an alternative embodiment, however, the product can contain different thermochromic dyes all having the same color. As the temperature of the composition is increased, however, the shade or intensity of the color can change. For instance, the product can change from a vibrant blue to a light blue to a clear color during normal washing.

In addition to the above, it should be understood that many alterations and permutations are possible. Any of a variety of colors and shades can be mixed in order to undergo color changes as a function of temperature.

In one particular embodiment, a plurality of thermochromic agents are configured to cause the cleansing product to change color over a temperature range of at least about 3° C. (5.4° F.), such as at least about 5° C. (9° F.), once the product is heated to a selected temperature. For example, multiple thermochromic agents may be present within the cleansing product so that the agents change color as the composition gradually increases in temperature. For instance, in one embodiment, a first thermochromic agent may be present that changes color at a temperature of from about 23° C. (73.4° F.) to about 28° C. (82.4° F.) and a second thermochromic agent may be present that changes color at a temperature of from about 27° C. (80.6° F.) to about 32° C. (89.6° F.). If desired, a third thermochromic agent may also be present that changes color at a temperature of from about 31° C. (87.8° F.) to about 36° C. (96.8° F.). In this manner, the cleansing product changes color at the selected temperature and then continues to change color in a stepwise manner as the temperature of the product continues to increase.

The plurality of thermochromic agents may be selected so that the color change occurs over a specific amount of time based upon the predicted increase in temperature of the cleansing product. For instance, the plurality of thermochromic agents may be selected so that under normal use conditions, the color change occurs over a time of from about 15 seconds to about 5 minutes and, suitably, from about 15 seconds to about 45 seconds. Once the cleansing product stops changing color, a user then knows that they have spent an appropriate amount of time washing, scrubbing or wiping.

As noted above, the cleansing product of the present disclosure additionally includes a cleansing composition. Generally, the cleansing composition for use in the cleansing product can contain one or more surfactants. When the cleansing product is for use in cleaning a part of a user's body, it is desirable to further include one or more emollients in the cleansing composition. In addition, the cleansing composition can contain sequestrants, non-aqueous solvents, preservatives, pH modifiers, anti-microbial agents, disinfectants, and various other optional ingredients.

As described above, the cleansing composition includes one or more surfactants. Preferably, in one embodiment, the surfactants are anhydrous surfactants or nearly anhydrous surfactants as to avoid including excess water, which can lead to premature swelling of the cleansing product. In another embodiment, the surfactant for use in the cleansing composition may be a high active surfactant; that is a surfactant being from about 70% to about 80% active. High active surfactants may include from about 10% (by weight) water to about 30% (by weight water). Nonionic surfactants, anionic surfactants, cationic surfactants, betaines, sultaines, amphoteric surfactants, zwitterionic surfactants, imidazolines, sulfosuccinates, amino oxides, alkanolamides, and combinations thereof may all be suitable for use in the present disclosure.

Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty (C-$C_{22}$) alcohol, including 3 to 20 ethylene oxide moieties, polyoxyethylene-20 isohexadecyl ether, polyoxyethylene-23 glycerol laurate, PEG 80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol 15-S-9) or 12 moles of ethylene oxide (Tergitol 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal CO-630 (a nonyl phenol ethoxylate) marketed by ISP Corp. (Wayne, N.J.). Suitable non-ionic ethoxylated octyl and nonyl phenols include those having from about 7 to about 13 ethoxy units.

Such compounds are commercially available under the trade name Triton X (Union Carbide, Danbury, Conn.).

Alkyl polyglycosides may also be used as a nonionic surfactant in the present cleansing compositions. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% $C_9$-$C_{11}$ alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler, Pa.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl) cocoamine oxide, bis(2-hydroxyethyl) tallow amine oxide, and bis(2-hydroxyethyl) stearylamine oxide. Moreover, still other useful amine oxides include those characterized as alkylamidopropyl di(lower alkyl) amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago, Ill.).

In addition to nonionic surfactants, the cleansing composition may also contain other types of surfactants. For instance, in some embodiments, amphoteric surfactants, such as zwitterionic surfactants, may also be used. For instance, one class of amphoteric surfactants that may be used in the present disclosure are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N, N-bis(2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium lauryl sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, cocamidopropyl betaine, lauric myristic amido propyl monosodium phosphitaine, and mixtures thereof.

In certain instances, it may also be desired to utilize one or more anionic surfactants within the cleansing composition. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The surfactants for use in the cleansing composition can be in any one of various forms including liquid surfactants, particulate surfactants, flake surfactants, and semi-solid or paste-like surfactants. Particularly preferred surfactants for use in the cleansing composition include, for example, particulate surfactants, such as disodium laury sulfosuccinate; flake surfactants, such as sodium coco-sulfate and sodium cocoyl taurate; and semi-solid surfactants, such as sodium cocoyl isethioniate.

The amount of surfactant contained in the cleansing composition can vary greatly depending upon various factors. Typically, the cleansing composition can contain surfactants in an amount of from about 0.1% (by weight cleansing composition) to about 50% (by weight cleansing composition). More suitably, the surfactant is present in the cleansing composition in an amount of from about 1% (by weight cleansing composition) to about 40% (by weight cleansing composition) and, even more suitably, from about 5% (by weight cleansing composition) to about 30% (by weight cleansing composition).

In addition to the surfactant, the cleansing composition can also include various emollients, moisturizers, humectants, and the like. In fact, some of the above described surfactants may be considered emollients. Particular emollients that may be used include ethoxylated and propoxylated alcohols, such as cetyl alcohols and ethoxylated lanolin. Particular humectants could be, but not be limited to glycerin, betaine, hyaluronic acid, sorbitol, and the like. Particular emollients and moisturizers could include, but are not to be limited to, natural oils such as jojoba oil, synthetic oils such as mineral oil, silicones such as dimethicone, fatty alcohols and acids such as cetyl alcohol and stearic acid, waxes such as beeswax, and the like. One skilled in the art will recognize that this list is not all inclusive and could include any other suitable materials commonly known in the art or referenced in the CTFA Ingredient Dictionary.

In one embodiment, the cleansing composition may further comprise other additional additives to improve a functional or physical property of the composition. For example, when the cleansing product is configured for use on hard, inanimate surfaces such as a bathtub, the cleansing composition for use in the cleansing product may further include a disinfectant. Examples of some suitable disinfectants for use in the cleansing compositions can include sodium dichloro-s-triazinetrione dihydrate, sodium hypochlorite, sodium perborate, percarbonate, perphosphate, and combinations thereof.

Typically, when a disinfectant is used, the cleansing composition can include from about 3% (by total weight cleansing composition) to about 15% (by total weight cleansing composition) disinfectant. More suitably, the cleansing composition can include from about 5% (by total weight cleansing composition) to about 9% (by total weight cleansing composition) disinfectant.

In one embodiment, the disinfectant can be used in the cleansing composition in combination with an oxygen bleach activator such as Tetraacetylethylenediamine (TAED).

In addition to the disinfectant, when used on hard, inanimate surfaces, the cleansing composition may further include abrasives, such as sodium carbonate, calcium carbonate, pumice, and the like. Furthermore, the cleansing composition may include builders, such as tripolyphosphate, acrylic homo and copolymers, and the like.

Another additive for use in the cleansing composition may be one or more non-aqueous solvents. Although not required, non-aqueous solvents can sometimes aid in dissolving certain components (e.g., preservatives, anti-microbial agent, etc.). Examples of some suitable non-aqueous solvents include, but are not limited to, glycerine; glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Solvent combinations include a glycol, particularly hexylene and/or propylene glycol, and one or more lower alcohols, particularly isopropanol, n-propanol, and/or ethanol.

The cleansing composition can also include various preservatives to increase the shelf life of the composition. Some suitable preservatives that can be used in the present disclosure include, but are not limited to, Kathon CG, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative utilized in the cleansing composition can generally vary depending on the relative amounts of the other components present within the composition. For example, in some embodiments, the preservative is present in the cleansing composition in an amount between about 0.001% (by weight cleansing composition) to about 5% (by weight cleansing composition), in some embodiments between about 0.001% (by weight cleansing composition) to about 1% (by weight cleansing composition), and in some embodiments, between about 0.1% (by weight cleansing composition) to about 0.15% (by weight cleansing composition).

In general, the pH of the cleansing composition may be controlled to be within any desired range, depending on the target soil. For example, a cleansing composition targeting an oily or greasy soil will desirably have a more basic pH, such as, for example, a pH in the range of from about 8 to about 11. By contrast, a cleansing composition intended for use against soap scum or lime-scale, such as found on the surface of a bathtub, will desirably have an acidic pH, preferably in the range of from about 3.5 to about 6.0. For bodily cleansing, it is typically desirable to have a cleansing composition with a neutral pH. If necessary, various pH modifiers may be utilized in the cleansing composition to achieve the desired pH level. For instance, some examples of basic pH modifiers that may be used in the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, and alginic acid.

In one embodiment, the cleansing composition may additionally include one or more sequestrants. A sequestrant is a substance whose molecules can form one or more bonds with a metal ion. In particular, water often contains metal ions, such as calcium ions, that might react with anionic components (e.g., surfactants, acids, etc.) present within the cleansing composition. For example, in one embodiment, a surfactant that remains substantially unreacted with metal ions can better function as a cleansing agent. Some examples of sequestrants that may be used in the cleansing composition of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

Typically, when one or more sequestrants are used in the cleansing compositions, the cleansing composition includes the sequestrants in an amount of from about 0.01% (by total weight cleansing composition) to about 2.0% (by total weight cleansing composition). More suitably, the cleansing composition includes from about 0.05% (by total weight cleansing composition) to about 1.0% (by total weight cleansing composition) sequestrant.

In order to better enhance the cleansing composition, other optional ingredients can also be used. For instance, some classes of ingredients that can be used include, but are not limited to: anti-microbial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (to increase the viscosity of the formulation).

Typically, as noted above, the cleansing products can be produced in any configuration known in the art. Specifically, in one preferred embodiment, the cleansing product includes the absorbent material, sponge material, polymeric network, coloring agent, and cleansing composition (and any one or more of the optional ingredients) each individually dispersed throughout the product. More particularly, the absorbent material and sponge material are located together and are thereby entrapped by the polymeric network. Furthermore, the cleansing composition and coloring agent are dispersed throughout the absorbent material, sponge material, and polymeric network. As noted above, the coloring agent can be encapsulated or configured to prevent premature activation upon contact with the surfactant in the cleansing composition.

In another embodiment, the cleansing product comprises layers, wherein each layer contains one or more of the components of the cleansing product. For example, in one particular embodiment, the cleansing product can comprise two separate and distinct layers. The first layer can include the absorbent material and polymeric network, and the second layer can include the sponge material. The coloring agent and cleansing composition can further be located in the first or second layers or can be include independently in both layers.

Typically, when the cleansing product comprises multiple layers, the layers are from about 0.5 millimeters (mm) to about 20 mm in thickness. More suitably, the cleansing product comprises layers having a thickness of from about 0.5 mm to about 10 mm.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above cleansing products without departing from the scope of the disclosure, it is intended that all matter contained in the above description shall be interpreted as illustrative and not in a limiting sense.

What is claimed is:

1. A cleansing product for bodily cleansing, the cleansing product comprising: an absorbent material, a polymeric network, an exfolliant agent, and a cleansing composition, the polymeric network being present in an amount of no greater than 50% (by total weight product), the cleansing composition comprising a surfactant, wherein the cleansing product is capable of expanding to a size of from about 80% to about 100% of its final expanded volume when contacted with warm water having a temperature of from about 19° C. to about 65° C. in no sooner than about 10 seconds, and wherein the polymeric network comprises polymers selected from the group consisting of modified starches, styrene maleic anhydride copolymer, metal salt neutralized ethylene methacrylic acid copolymer, polyether-block-polyurethane, polyethyloxazoline, water-soluble polyurethane, and combinations thereof, and wherein the cleansing product further comprises a sponge material, the sponge material comprising melamine-foam material.

2. The cleansing product as set forth in claim 1 wherein the absorbent material comprises a material selected from the group consisting of nonwoven webs, woven materials, knit materials, wet-strength papers, and combinations thereof.

3. The cleansing product as set forth in claim 1 wherein the absorbent material further comprises a superabsorbent material.

4. The cleansing product as set forth in claim 3 wherein the superabsorbent material is present in the absorbent material of the cleansing product in an amount of from about 0.1% (by total weight absorbent material) to about 20% (by total weight absorbent material).

5. The cleansing product as set forth in claim 1 wherein the polymeric network comprises a polymer having a glass transition temperature of at least about 20° C.

6. The cleansing product as set forth in claim 1 wherein the polymeric network further comprises a plasticizing agent.

7. The cleansing product as set forth in claim 1 wherein the absorbent material further comprises an elastomeric random block polymer.

8. The cleansing product as set forth in claim 1 wherein the exfolliant agent is selected from the group consisting of an exfolliant disc, an exfolliant ridge, or exfolliant particles embedded into an outer surface of the cleansing product.

9. A cleansing product for bodily cleansing, the cleansing product comprising: an absorbent material, a polymeric network, an exfolliant agent, a coloring agent, and a cleansing composition, the polymeric network being present in an amount of no greater than 50% (by total weight product), the cleansing composition comprising a surfactant, wherein the cleansing product is capable of expanding to a size of from about 80% to about 100% of its final expanded volume when contacted with warm water having a temperature of from about 19° C. to about 65° C. in no sooner than about 10 seconds, wherein the coloring agent is capable of changing the color of the cleansing product when the cleansing product is contacted with warm water in no sooner than 15 seconds, and wherein the polymeric network comprises polymers selected from the group consisting of modified starches, styrene maleic anhydride copolymer, metal salt neutralized ethylene methacrylic acid copolymer, polyether-block-polyurethane, polyethyloxazoline, water-soluble polyurethane, and combinations thereof, and wherein the cleansing product further comprises a sponge material, the sponge material comprising melamine-foam material.

10. The cleansing product as set forth in claim 9 wherein the absorbent material comprises a material selected from the group consisting of nonwoven webs, woven materials, knit materials, wet-strength papers, and combinations thereof.

11. The cleansing product as set forth in claim 9 wherein the absorbent material further comprises a superabsorbent material.

12. The cleansing product as set forth in claim 9 wherein the polymeric network comprises a polymer having a glass transition temperature of at least about 20° C.

13. The cleansing product as set forth in claim 9 wherein the polymeric network further comprises a plasticizing agent.

14. The cleansing product as set forth in claim 9 wherein the absorbent material further comprises an elastomeric random block polymer.

* * * * *